United States Patent
Konda et al.

(10) Patent No.: US 10,987,484 B1
(45) Date of Patent: Apr. 27, 2021

(54) BABY MONITOR SYSTEM SOUND AND LIGHT DELIVERY BASED ON VITALS

(71) Applicant: SYNERGEN Technology Labs, LLC, Dallas, TX (US)

(72) Inventors: Sunil Konda, Dallas, TX (US); Mel Gunawardena, Dallas, TX (US); Pradeep Pathirana, Dallas, TX (US); Prabath Gallage, Dallas, TX (US)

(73) Assignee: SYNERGEN Technology Labs, LLC, Dallas, TX (US)

( * ) Notice: Subject to any disclaimer, the term of this patent is extended or adjusted under 35 U.S.C. 154(b) by 0 days.

(21) Appl. No.: 16/885,030

(22) Filed: May 27, 2020

(51) Int. Cl.
*A61K 41/00* (2020.01)
*A61N 5/10* (2006.01)
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0044* (2013.01); *A61M 2205/3306* (2013.01); *A61M 2230/18* (2013.01); *A61M 2230/205* (2013.01)

(58) Field of Classification Search
CPC . A61B 5/0816; A61B 5/4812; A61B 5/14542; A61B 5/14551; A61B 5/16; A61B 5/4815
See application file for complete search history.

(56) References Cited

U.S. PATENT DOCUMENTS

| | | | |
|---|---|---|---|
| 7,041,049 B1* | 5/2006 | Raniere | A61M 21/02 128/905 |
| 2005/0124864 A1 | 6/2005 | Mack et al. | |
| 2010/0041966 A1 | 2/2010 | Kang et al. | |
| 2013/0208576 A1* | 8/2013 | Loree, IV | G04G 11/00 368/256 |
| 2014/0316191 A1 | 10/2014 | de Zambotti et al. | |
| 2017/0312476 A1 | 11/2017 | Woo | |
| 2018/0110959 A1* | 4/2018 | Cronin | A61B 5/6801 |
| 2019/0059807 A1 | 2/2019 | Su et al. | |
| 2019/0200872 A1* | 7/2019 | Matsuoka | A61B 5/0013 |

FOREIGN PATENT DOCUMENTS

| | | |
|---|---|---|
| CN | 108903152 A | 11/2018 |
| KR | 20130005802 A | 1/2013 |
| WO | 2018175642 A1 | 9/2018 |
| WO | 2019077120 A1 | 4/2019 |

* cited by examiner

*Primary Examiner* — Christine H Matthews
*Assistant Examiner* — Joshua Daryl D Lannu
(74) *Attorney, Agent, or Firm* — Conley Rose, P.C.

(57) ABSTRACT

A baby monitor system comprises: a memory; and a processor coupled to the memory and configured to: obtain a sleep schedule of a baby; obtain vitals of the baby, wherein the vitals are based on pulse oximetry; and cause a first sound or a first light to emit in response to the sleep schedule and the vitals. A method comprises: obtaining a sleep schedule of a baby; obtaining vitals of the baby, wherein the vitals are based on pulse oximetry; and causing a first sound or a first light to emit in response to the sleep schedule and the vitals.

23 Claims, 6 Drawing Sheets

FIG. 6

BABY MONITOR SYSTEM SOUND AND LIGHT DELIVERY BASED ON VITALS

CROSS-REFERENCE TO RELATED APPLICATIONS

Not applicable.

BACKGROUND

Baby monitors have existed for almost a century. Originally, baby monitors used one-way audio from a baby to a parent so that the parent could monitor sounds from the baby. Subsequent baby monitors incorporated two-way audio so that the parent could also speak to the baby. Eventually, baby monitors added one-way video from the baby to the parent so that the parent could monitor movement and other behavior of the baby. The next generation of baby monitors is incorporating features to ensure baby safety.

SUMMARY

In a first embodiment, a baby monitor system comprises: a memory; and a processor coupled to the memory and configured to: obtain a sleep schedule of a baby; obtain vitals of the baby, wherein the vitals are based on pulse oximetry; and cause a first sound or a first light to emit in response to the sleep schedule and the vitals.

In a second embodiment, a method comprises: obtaining a sleep schedule of a baby; obtaining vitals of the baby, wherein the vitals are based on pulse oximetry; and causing a first sound or a first light to emit in response to the sleep schedule and the vitals.

In a third embodiment, a computer program product comprises computer-executable instructions for storage on a non-transitory computer-readable medium that, when executed by a processor, cause an apparatus to: obtain a sleep schedule of a baby; obtain vitals of the baby, wherein the vitals are based on pulse oximetry; and cause a first sound or a first light to emit in response to the sleep schedule and the vitals.

Any of the above embodiments may be combined with any of the other above embodiments to create a new embodiment. These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The following abbreviations apply:
ASIC: application-specific integrated circuit
CPU: central processing unit
DSP: digital signal processor
EO: electrical-to-optical
FPGA: field-programmable gate array
LAN: local area network
lm: lumen(s)
OE: optical-to-electrical
RAM: random-access memory
REM: rapid eye movement
RF: radio frequency
ROM: read-only memory
RX: receiver unit
SIDS: sudden infant death syndrome
SRAM: static RAM
TCAM: ternary content-addressable memory
TX: transmitter unit.

Current baby monitors monitor baby vital signs, which may be simply referred to as vitals. For instance, some baby monitors use pulse oximetry to determine a baby's oxygen saturation and heart rate. The oxygen saturation and the heart rate can indicate the baby's sleep status, as well as unwanted events such as suffocation, an infection, and sleep apnea. Baby monitors may also include temperature sensors to measure the baby's body temperature. Thus, baby monitors can be powerful tools important information about sleep status and unwanted events. While such baby monitors may help ensure the baby's safety, they do not assist with the baby's sleep.

Disclosed herein are embodiments for baby monitor system sound and light delivery based on vitals. The baby monitor system comprises a wearable that obtains vitals from a baby using pulse oximetry and a base station that delivers sound and light based on those vitals. The sound and light guide a baby into and out of sleep. If the baby prematurely awakes, then the base station may repeat the process. While pulse oximetry is discussed, the wearable may employ other techniques to obtain vitals. In addition, though a baby and a parent are discussed, the baby monitor system may be a more general system that assists children and their parents, adults and their caretakers, or others.

Figure 1:
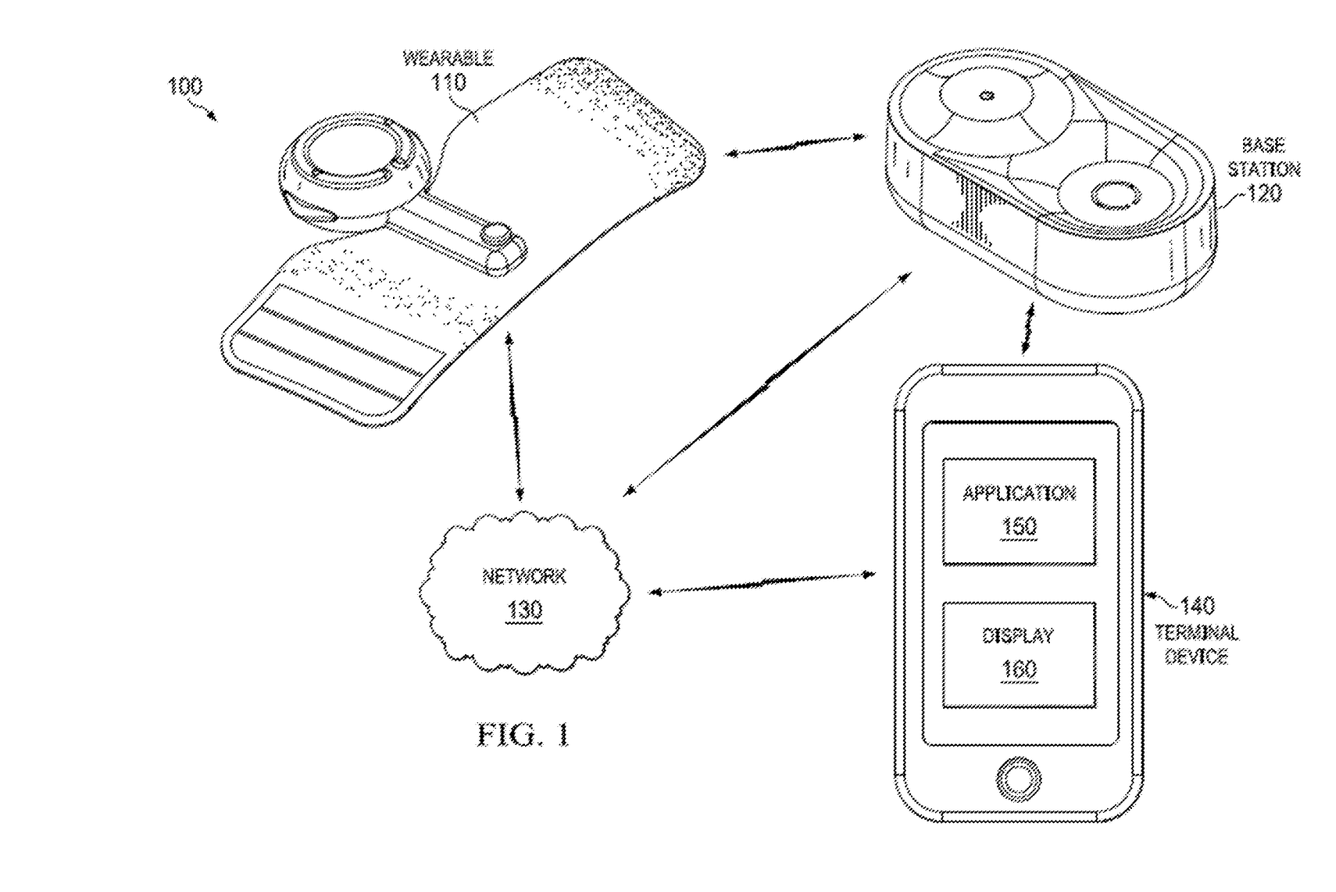
FIG. 1 is a baby monitor system according to an embodiment of the disclosure.

FIG. 1 is a baby monitor system 100 according to an embodiment of the disclosure. The baby monitor system 100 comprises a wearable 110, a base station 120, a network 130, and a terminal device 140. The network 130 is the Internet, a LAN, or another suitable network. Though the terminal device 140 is shown as a mobile phone, the terminal device 140 is any device suitable for communicating with the network 130. The terminal device 140 comprises an application 150 and a display 160.

The wearable 110 obtains vitals from a baby using pulse oximetry. The vitals comprise oxygen saturation and heart rate. The wearable may obtain vitals using other techniques such as temperature sensing. Thus, the vitals may also comprise body temperature. The wearable 110 transmits the vitals to the base station 120 either directly using Bluetooth or another suitable technology or indirectly through the network 130.

The base station 120 receives the vitals from the wearable 110, emits sound and light based on the vitals, and transmits information to the terminal device 140 either directly using Bluetooth or another suitable technology or indirectly through the network 130. The base station 110 may emit the sound and the light also based on audio data, video data, or velocity data. The information includes information about the sound, the light, and the vitals.

The terminal device 140 receives the information through the application 150 and displays the information on the display 160. A parent views the information and generates first instructions using the application 150. The terminal device 140 transmits first instructions to the base station 120 either directly using Bluetooth or another suitable technology or indirectly through the network 130. The base station 120 processes the first instructions, generates second instructions based on the first instructions, and transmits the second instructions to the wearable 110. The wearable 110 receives and implements the second instructions.

Figure 2A:
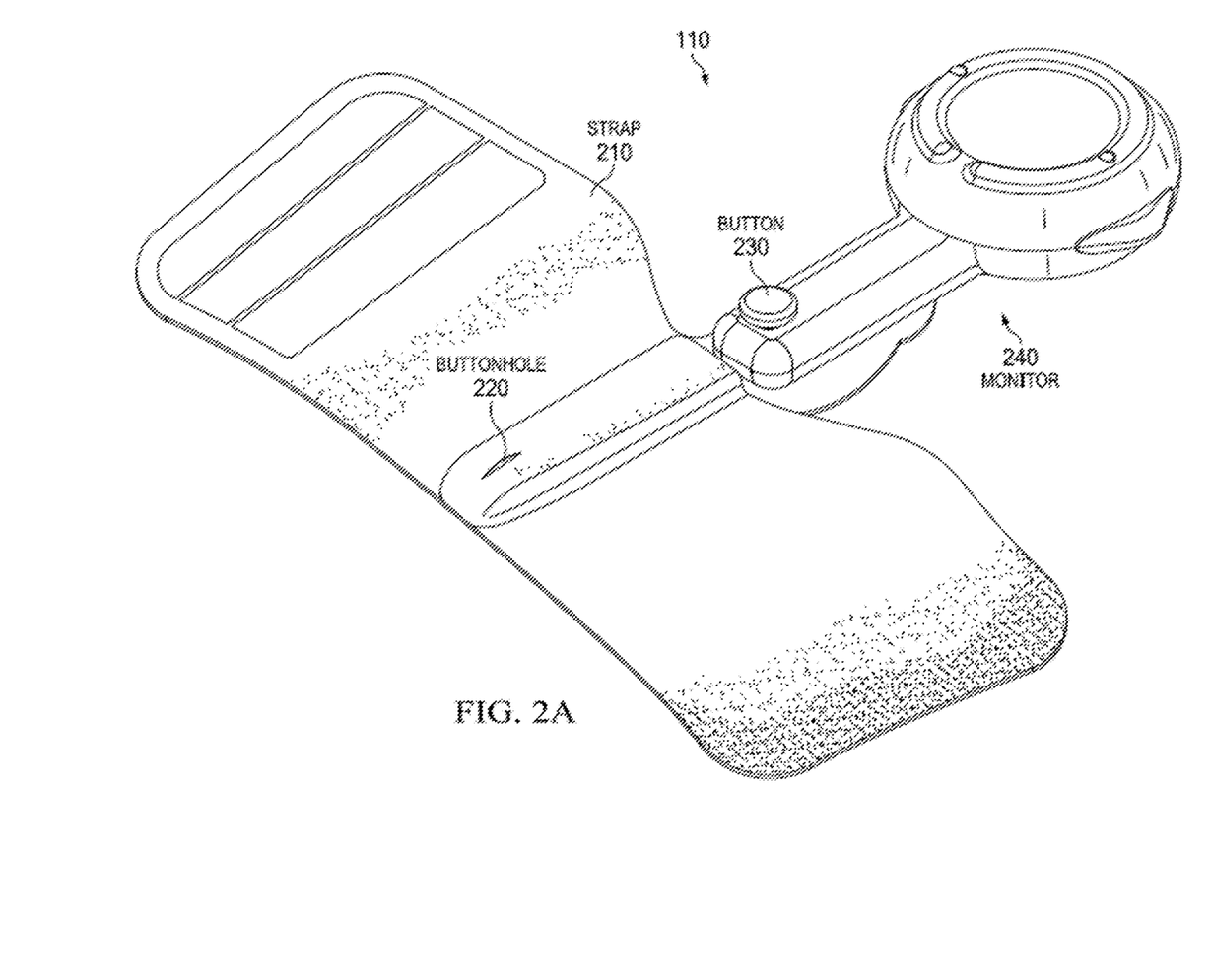
FIG. 2A is a top perspective view of the wearable in FIG. 1.

FIG. 2A is a top perspective view of the wearable 110 in FIG. 1. FIG. 2A shows that the wearable 110 comprises a strap 210, a buttonhole 220, and a monitor 240. The monitor 240 comprises a button 230. The strap 210 wraps around the baby's foot, ankle, or leg to secure the wearable 110 to the baby. The buttonhole 220 secures the button 230, and thus the monitor 240, to the strap 210.

Figure 2B:
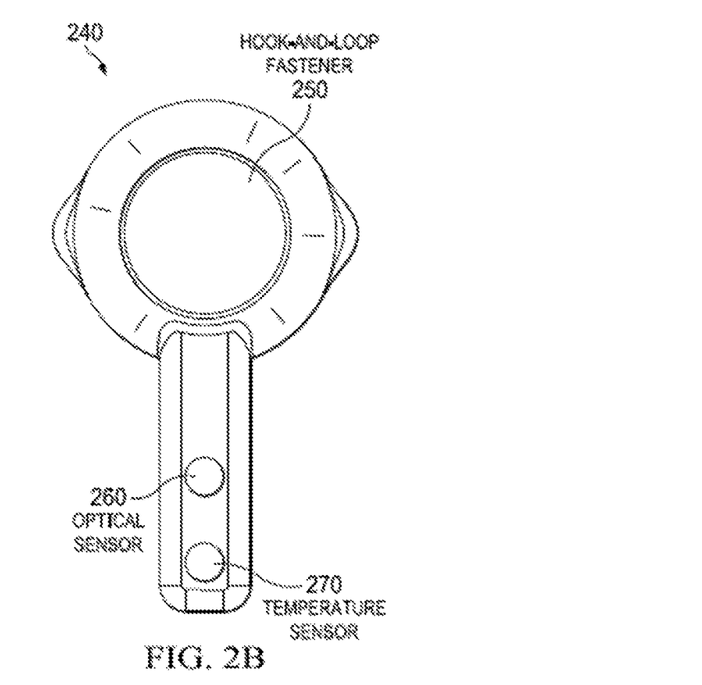
FIG. 2B is a top view of the monitor in FIG. 2A.

FIG. 2B is a top view of the monitor 240 in FIG. 2A. FIG. 2B shows that the monitor 240 comprises a hook-and-loop fastener 250, an optical sensor 260, and a temperature sensor 270. The hook-and-loop fastener 250 secures the monitor 240 within the strap 210 and against the baby. The optical sensor 260 performs pulse oximetry through the skin of the baby. The temperature sensor 270 obtains the temperature of the baby's body.

Figure 3A:
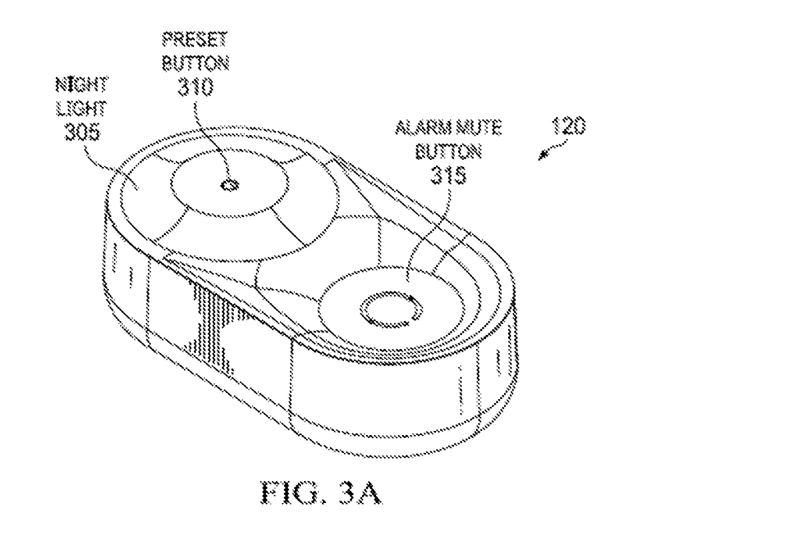
FIG. 3A is a front perspective view of the base station in FIG. 1.

FIG. 3A is a front perspective view of the base station 120 in FIG. 1. FIG. 3A shows that the base station 120 comprises a night light 305, a preset button 310, and an alarm mute button 315. The night light 305 emits light. The preset button 310 toggles presets on and off. The presets may include customizable light and sound settings. For instance, each preset may include a color and an intensity of the light, a music or white noise selection, and audio levels for the sound. The presets may also include days, start times, and end times for the sound and the light, for instance as part of a sleep schedule as described below. A manufacturer of the base station 120 or another company may pre-configure the presets in, or push the presets to, the base station 120. The presets may be based on recommendations from sleep experts. The alarm mute button 315 mutes an alarm that plays from the base station 120.

Figure 3B:
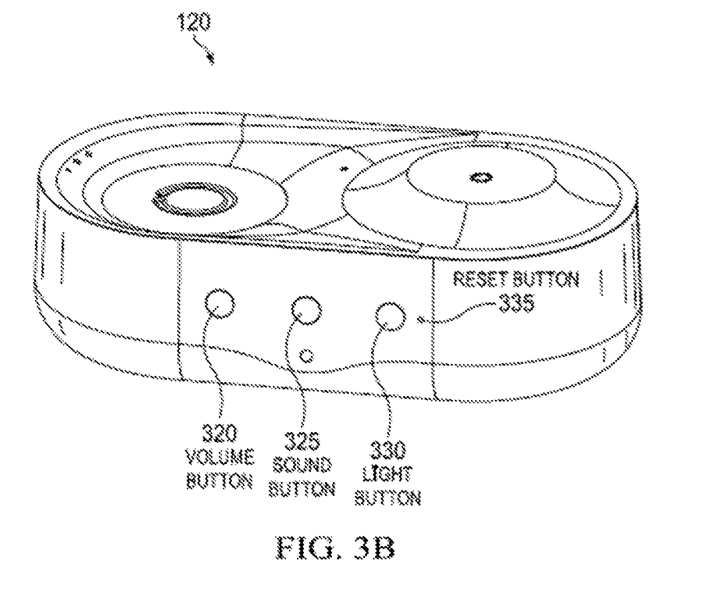
FIG. 3B is a back perspective view of the base station in FIG. 1.

FIG. 3B is a back perspective view of the base station 120 in FIG. 1. FIG. 3B shows that the base station 120 further comprises a volume button 320, a sound button 325, a night light button 330, and a reset button 335. The volume button 320 adjusts a volume of sound emitting from the base station 120. The sound button 325 plays or pauses the sound emitting from the base station 120. The night light button 330 turns off, turns on, or adjusts light emitting from the night light 305. The reset button 335 resets the base station 120.

Figure 3C:
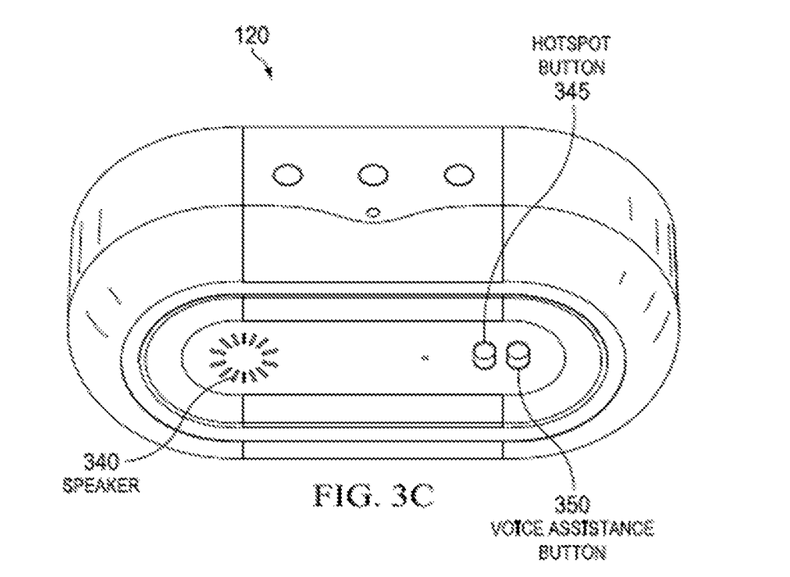
FIG. 3C is a bottom view of the base station in FIG. 1.

FIG. 3C is a bottom view of the base station 120 in FIG. 1. FIG. 3C shows that the base station 120 further comprises a speaker 340, a hotspot button 345, and a voice assistance button 350. The speaker 340 emits sound. The hotspot button 345 toggles on and off a wireless hotspot. The parent may use may use the hotspot to set up or configuration the wearable 110 and the base station 120. The voice assistance button 350 turns on and off a voice assistant such as Amazon Alexa or Google Home.

The baby monitor system 100 implements various modes. Those modes include a sound mode and a light mode. The parent may customize those modes at any time through the application 150.

Sound Mode

Some babies sleep better in response to sound. The sound may assist the baby in going to sleep or staying asleep. The sound may be background noise such as white noise or music such as lullabies or classical music, depending on the baby's preference. The baby monitor system 100 delivers such sound.

In a sound mode, the speaker 340 emits a first sound in order to assist the baby's sleep. The first sound may be background noise or music. The speaker 340 begins emitting the first sound at a first predetermined time, in response to a manual toggle of the sound button 325, or in response to a manual instruction in the application 150. The first predetermined time may be when the baby is to begin sleep. For instance, the parent sets the first predetermined time to 7:00 p.m. using the application 150. In this context, "predetermined" means before an associated operation is to be executed. Thus, the first predetermined time is set before the speaker 340 begins emitting the first sound at the first predetermined time.

The speaker 340 gradually increases a volume of the first sound until the volume is a first predetermined volume or until the baby falls asleep. The base station 120 knows when the baby is asleep based on the vitals the base station 120 receives from the wearable 110. Once the baby is asleep, the speaker 340 gradually decreases the volume of the first sound until the volume is a second predetermined volume or until the baby reaches a predetermined state of sleep. For instance, the predetermined state of sleep is a REM state. The base station 120 knows when the baby is in the predetermined state of sleep based on the vitals the base station 120 receives from the wearable 110.

If the baby prematurely awakes, then the speaker 340 repeats the process above to guide the baby back to sleep. Premature awakening may be defined as any time before a second predetermined time, which is described below. The base station 120 knows when the baby prematurely awakes based on the vitals the base station 120 receives from the wearable 110. The base station 120 may know when the baby prematurely awakes also based on audio data, video data, or velocity data, which are described further below.

Finally, the speaker 340 begins emitting a second sound at the second predetermined time. The second predetermined time may be when the baby is to wake up. For instance, the parent sets the second predetermined time to 7:00 a.m. using the application 150. A type and volume of the second sound may be set to ensure that the baby awakes. The speaker 340 ends emitting the second sound until a predetermined time or until the baby reaches a predetermined state of arousal. The base station 120 knows a current state of arousal based on the vitals the base station 120 receives from the wearable 110.

In addition, the parent may manually toggle off and on or adjust the volume of the first sound or the second sound at any time using the volume button 320, the sound button 325, or the application 150. For instance, the parent increases the volume of the second sound in order to mask a loud noise such as a car alarm that might interrupt the baby's sleep. The speaker 340 may emit different sounds corresponding to different sleep states. For instance, the first sound may begin as a lullaby and end as white noise. The speaker 340 may vary the sounds and the sounds' volumes based on environmental data. For instance, the sounds may be louder if ambient noise is louder. The base station 120 may collect data related to the baby's sleep patterns, identify trends, and make suggestions to the parent. For instance, the base station 120 may suggest what sounds and volumes yield the best sleep for the baby, and the parent may select those sounds and volumes. When the video data indicate that the baby has exited the bed or the audio data indicate include certain known words, the speaker 340 may emit pre-recorded voices of parents or emit other sounds to calm or instruct the baby.

Light Mode

Some babies sleep better in response to light. The light may assist the baby in going to sleep. For instance, the baby may feel comforted knowing that a light is on. The baby monitor system 100 delivers such light.

In a light mode, the night light 305 emits a first light in order to assist the baby's sleep. The first light may be a red light, which may aid or at least not inhibit sleep, yet comfort the baby. The red light may be relatively dim. For instance, the red light is about 0-12 lm. The night light 305 begins emitting the first light at a first predetermined time, in response to a manual toggle of the night light button 330, or in response to a manual instruction in the application 150. The first predetermined time may be when the baby is to sleep. For instance, the parent sets the first predetermined time to 7:00 p.m. using the application 150. Once the baby is asleep, the night light 305 stops emitting the first light. The base station 120 knows when the baby is asleep based on the vitals the base station 120 receives from the wearable 110.

If the baby prematurely awakes, then the night light 305 repeats the process above to guide the baby back to sleep. Again, premature awakening may be defined as any time before a second predetermined time, which is described below. The base station 120 knows when the baby prematurely awakes based on the vitals the base station 120 receives from the wearable 110.

Finally, the night light 305 emits a second light at the second predetermined time. The second light may be a white light, which may arouse the baby. The white light may be relatively bright. For instance, the white light is about 0-25 lm. The second predetermined time may be when the baby is to wake up. For instance, the parent sets the second predetermined time to 7:00 a.m. using the application 150. Premature awakening may be defined as any time before the second predetermined time.

In addition, the parent may manually toggle off and on or adjust the amount of the first light or the second light at any time using the night light button 330 or the application 150. For instance, in the case of an older child who is potty training, the parent may toggle on the night light 305 if the child indicates that he or she needs to go to the bathroom, and the night light 305 may comfort the child and assist his or her ability to see a way to the bathroom. Similarly, data from the optical sensor 260, audio data, video data, or velocity data may indicate whether the child has stepped out of the bed for another reason. In response, the parent may toggle on the night light 305 to assist the child. The base station 120 may be programmed to respond to certain words spoken by the child, for example, "mom," "dad," or "potty," by turning on or off the night light 305, changing an intensity of the light, or changing a color of the light.

Figure 4:
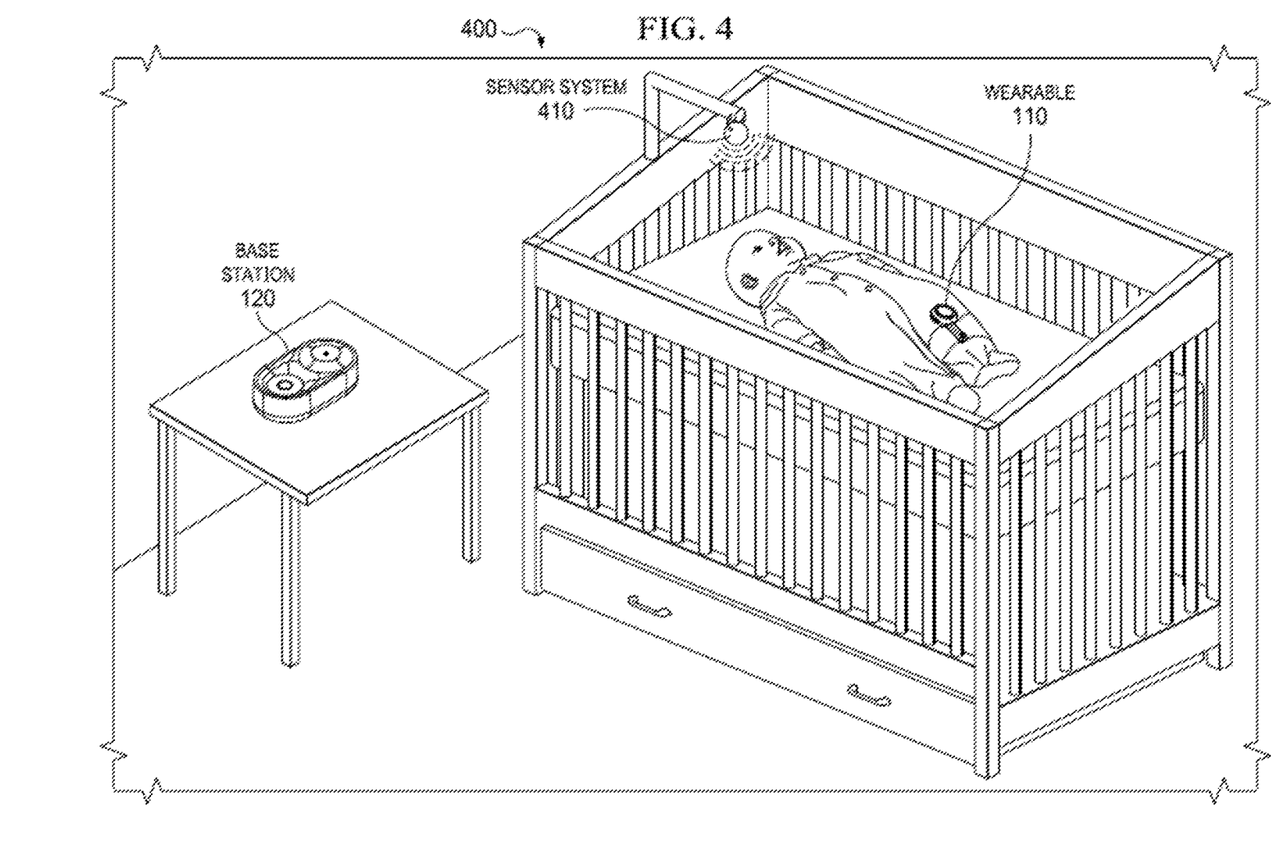
FIG. 4 is a baby monitor environment according to an embodiment of the disclosure.

FIG. 4 is a baby monitor environment 400 according to an embodiment of the disclosure. The baby monitor environment 400 comprises the base station 120, a sensor system 410, and the wearable 110. The sensor system 410 comprises a microphone that obtains audio data; a camera that obtains video data; a Doppler radar that obtains velocity data; and a transmitter that transmits the audio data, the video data, and the velocity data to the base station 120. The base station 120 may emit the sound and the light based on the audio data, the video data, or the velocity data as described above. Though not shown, the baby monitor environment 400 may further comprise the network 130 and the terminal device 140 and thus comprise the larger baby monitor system 100.

Figure 5:
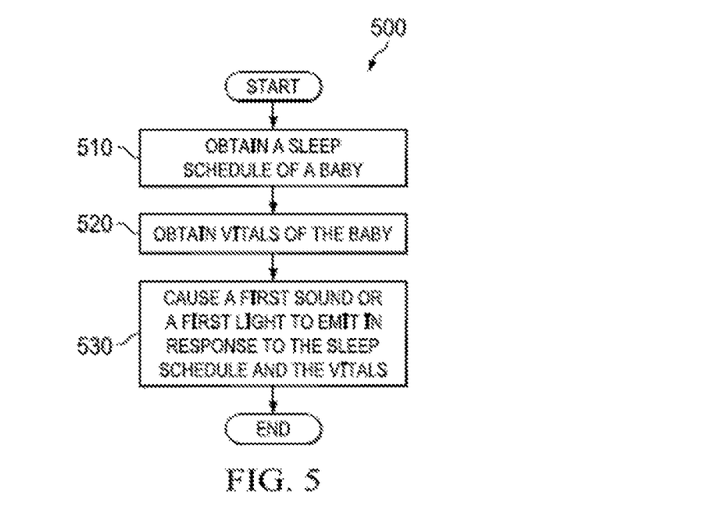
FIG. 5 is a flowchart illustrating a method of baby monitor system sound and light delivery based on vitals according to an embodiment of the disclosure.

FIG. 5 is a flowchart illustrating a method 500 of baby monitor system sound and light delivery based on vitals according to an embodiment of the disclosure. The baby monitor system 100 implements the method 500. Specifically, the base station 120 may implement the method 500.

At step 510, a sleep schedule of a baby is obtained. For instance, the base station 120 obtains the sleep schedule from the parent through the application 150. The sleep schedule may comprise a first predetermined time when the baby is to begin sleep, a predetermined state of sleep such as a REM state, and a second predetermined time when the baby is to wake up. Alternatively, the sleep schedule is a manual toggle using the sound button 325, the night light button 330, or the application 150.

At step 520, vitals of the baby are obtained. For instance, the base station 120 obtains vitals from the wearable 110. The vitals may be based on pulse oximetry using the optical sensor 260. The vitals may comprise oxygen saturation and heart rate.

Finally, at step 530, a first sound or a first light is caused to be emitted in response to the sleep schedule and the vitals. The first sound may be music or white noise. The first light may be a red light or a dim red light.

The method 500 may comprise additional steps. The first sound may be further caused to emit at a first predetermined time when the baby is to begin sleep or in response to a manual toggle or a manual instruction. A volume of the first sound may be caused to increase until the volume is a first predetermined volume or until the baby falls asleep. After the baby is asleep, the volume may be caused to decrease until the volume is a second predetermined volume or until the baby reaches a predetermined state of sleep. The first light may be further caused to emit at a first predetermined time when the baby is to begin sleep or in response to a manual toggle or a manual instruction. Finally, after the baby is asleep, the first light may be caused to stop emitting.

Figure 6:
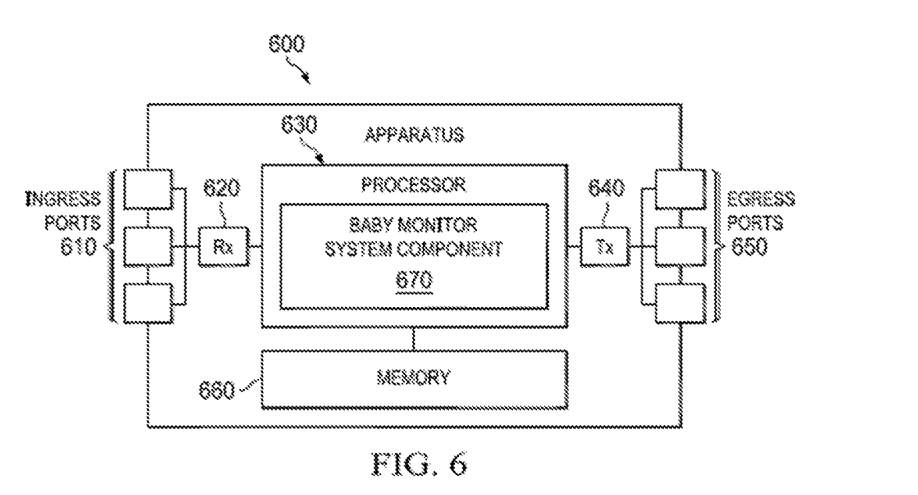
FIG. 6 is a schematic diagram of an apparatus according to an embodiment of the disclosure.

FIG. 6 is a schematic diagram of an apparatus 500 according to an embodiment of the disclosure. The apparatus 600 may implement the disclosed embodiments. The apparatus 600 comprises ingress ports 610 and an RX 620 to receive data; a processor, 630 or logic unit, baseband unit, CPU, or processing means to process the data; a TX 640 and egress ports 650 to transmit the data; and a memory 660 to store the data. The apparatus 600 may also comprise OE components, EO components, or RF components coupled to the ingress ports 610, the RX 620, the TX 640, and the egress ports 650 to provide ingress or egress of optical signals, electrical signals, or RF signals.

The processor 630 is any combination of hardware, middleware, firmware, or software. The processor 630 comprises any combination of one or more CPU chips, cores, FPGAs, ASICs, or DSPs. The processor 630 communicates with the ingress ports 610, the RX 620, the TX 640, the egress ports 650, and the memory 660. The processor 630 comprises a baby monitor system component 670, which implements the disclosed embodiments. The inclusion of the baby monitor system component 670 therefore provides a substantial improvement to the functionality of the apparatus 600 and effects a transformation of the apparatus 600 to a different state. Alternatively, the memory 660 stores the baby monitor system component 670 as instructions, and the processor 630 executes those instructions.

The memory 660 comprises any combination of disks, tape drives, or solid-state drives. The apparatus 600 may use the memory 660 as an over-flow data storage device to store programs when the apparatus 600 selects those programs for execution and to store instructions and data that the apparatus 600 reads during execution of those programs, for instance as a computer program product. The memory 660 may be volatile or non-volatile and may be any combination of ROM, RAM, TCAM, or SRAM.

A computer program product may comprise computer-executable instructions stored on a non-transitory medium that, when executed by a processor, cause an apparatus to perform the disclosed embodiments. The non-transitory medium may be the memory 660. The processor may be the processor 630. The apparatus may be the apparatus 600.

In a first aspect, a baby monitor system comprises: a memory; and a processor coupled to the memory and configured to: obtain a sleep schedule of a baby; obtain vitals of the baby, wherein the vitals are based on pulse oximetry; and cause a first sound or a first light to emit in response to the sleep schedule and the vitals.

In a second aspect based on the first aspect, the baby monitor system further comprises a base station, wherein the base station comprises the memory and the processor.

In a third aspect based on any of the first through second aspects, the base station further comprises a speaker configured to emit the first sound.

In a fourth aspect based on any of the first through third aspects, the baby monitor system further comprises a wearable, wherein the wearable comprises an optical sensor configured to perform the pulse oximetry.

In a fifth aspect based on any of the first through fourth aspects, the processor is further configured to further cause the first sound to emit at a first predetermined time when the baby is to begin sleep or in response to a manual toggle or a manual instruction.

In a sixth aspect based on any of the first through fifth aspects, the processor is further configured to cause a volume of the first sound to increase until the volume is a first predetermined volume or until the baby falls asleep.

In a seventh aspect based on any of the first through sixth aspects, the processor is further configured to, after the baby is asleep, decrease the volume until the volume is a second predetermined volume or until the baby reaches a predetermined state of sleep.

In an eighth aspect based on any of the first through seventh aspects, the predetermined state is a REM state.

In a ninth aspect based on any of the first through eighth aspects, when the baby prematurely awakes, the processor is further configured to: cause the first sound to emit; cause the volume to increase until the volume is the first predetermined volume or until the baby falls asleep; and cause, after the baby is asleep, the volume to decrease until the volume is the second predetermined volume or until the baby reaches the predetermined state of sleep.

In a tenth aspect based on any of the first through ninth aspects, the processor is further configured to cause a second sound to emit at a second predetermined time when the baby is to wake up.

In an eleventh aspect based on any of the first through tenth aspects, the second predetermined time is when the baby is to wake up.

In a twelfth aspect based on any of the first through eleventh aspects, the processor is further configured to further cause the first light to emit at a first predetermined time when the baby is to begin sleep or in response to a manual toggle or a manual instruction.

In a thirteenth aspect based on any of the first through twelfth aspects, the processor is further configured to, after the baby is asleep, cause the first light to stop emitting.

In a fourteenth aspect based on any of the first through thirteenth aspects, when the baby prematurely awakes, the processor is further configured to: cause the first light to emit; and cause, after the baby is asleep, the first light to stop emitting.

In a fifteenth aspect based on any of the first through fourteenth aspects, the processor is further configured to cause a second light to emit at a second predetermined time when the baby is to wake up.

In a sixteenth aspect, a method comprises: obtaining a sleep schedule of a baby; obtaining vitals of the baby, wherein the vitals are based on pulse oximetry; and causing a first sound or a first light to emit in response to the sleep schedule and the vitals.

In a seventh aspect based on the sixteenth aspect, the method further comprises: further causing the first sound to emit at a first predetermined time when the baby is to begin sleep or in response to a manual toggle or a manual instruction; causing a volume of the first sound to increase until the volume is a first predetermined volume or until the baby falls asleep; and causing, after the baby is asleep, the volume to decrease until the volume is a second predetermined volume or until the baby reaches a predetermined state of sleep.

In an eighteenth aspect based on any of the sixteenth through seventeenth aspect, the method further comprises: further causing the first light to emit at a first predetermined time when the baby is to begin sleep or in response to a manual toggle or a manual instruction; and causing, after the baby is asleep, the first light to stop emitting.

In a nineteenth aspect, a computer program product comprises computer-executable instructions for storage on a non-transitory computer-readable medium that, when executed by a processor, cause an apparatus to: obtain a sleep schedule of a baby; obtain vitals of the baby, wherein the vitals are based on pulse oximetry; and cause a first sound or a first light to emit in response to the sleep schedule and the vitals.

In a twentieth aspect based on the nineteenth aspect, the instructions further cause the apparatus to: further cause the first sound to emit at a first predetermined time when the baby is to begin sleep or in response to a manual toggle or a manual instruction; cause a volume of the first sound to increase until the volume is a first predetermined volume or until the baby falls asleep; cause, after the baby is asleep, the volume to decrease until the volume is a second predetermined volume or until the baby reaches a predetermined state of sleep; further cause the first light to emit at the first predetermined time or in response to a manual toggle or a manual instruction; and cause, after the baby is asleep, the first light to stop emitting.

The terms "about," "approximately," and their derivatives mean within ±10% of a subsequent modifier. While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A baby monitor system comprising:
a memory; and
a processor coupled to the memory and configured to:
obtain a sleep schedule of a baby;
obtain vitals of the baby, wherein the vitals are based on pulse oximetry;
transmit, when the sleep schedule indicates that the baby is to begin sleep, a first electrical signal to cause an action, wherein the action is an emission of a first sound or a first light;
make, based on the vitals and after transmitting the first electrical signal, a first determination that the baby has fallen asleep;
transmit, in response to the first determination, a second electrical signal to adjust the action;
make, based on the vitals and after transmitting the second electrical signal, a second determination that the baby has reached a predetermined state of sleep;
transmit, in response to the second determination, a third electrical signal to further adjust or cancel the action;
make a third determination that the baby has prematurely awoken;
cause, in response to the third determination, the first sound to emit and a volume of the first sound to increase until the volume is a first predetermined volume or until the baby falls asleep again;
make a fourth determination that the baby has fallen asleep again; and
cause, in response to the fourth determination, the volume to decrease until the volume is a second predetermined volume or until the baby reaches the predetermined state again.

2. The baby monitor system of claim 1, further comprising a base station, wherein the base station comprises the memory and the processor.

3. The baby monitor system of claim 2, wherein the base station further comprises a speaker configured to emit the first sound.

4. The baby monitor system of claim 1, further comprising a wearable, wherein the wearable comprises an optical sensor configured to perform the pulse oximetry.

5. The baby monitor system of claim 1, wherein the processor is further configured to further transmit the third electrical signal to decrease the action.

6. The baby monitor system of claim 1, wherein the processor is further configured to further transmit the third electrical signal to cancel the action.

7. The baby monitor system of claim 1, wherein the action is the emission of the first sound.

8. The baby monitor system of claim 7, wherein the processor is further configured to cause a second sound to emit at a predetermined time.

9. The baby monitor system of claim 8, wherein the predetermined time is when the baby is to wake up.

10. The baby monitor system of claim 1, wherein the predetermined state is a rapid eye movement (REM) state.

11. The baby monitor system of claim 1, wherein the action is the emission of the first light.

12. The baby monitor system of claim 11, wherein the processor is further configured to further transmit the third electrical signal to cause the first light to stop emitting.

13. The baby monitor system of claim 12, wherein when the baby prematurely awakes, the processor is further configured to:
cause the first light to emit; and
cause, after the baby is asleep again, the first light to stop emitting.

14. The baby monitor system of claim 12, wherein the processor is further configured to cause a second light to emit at a predetermined time.

15. The baby monitor system of claim 14, wherein the predetermined time is when the baby is to wake up.

16. A method implemented by a baby monitor system and comprising:
obtaining a sleep schedule of a baby;
obtaining vitals of the baby, wherein the vitals are based on pulse oximetry;
transmitting, when the sleep schedule indicates that the baby is to begin sleep, a first electrical signal to cause an action, wherein the action is an emission of a first sound or a first light;
making, based on the vitals and after transmitting the first electrical signal, a first determination that the baby has fallen asleep;
transmitting, in response to the first determination, a second electrical signal to adjust the action;
making, based on the vitals and after transmitting the second electrical signal, a second determination that the baby has reached a predetermined state of sleep,
transmitting, in response to the second determination, a third electrical signal to further adjust or cancel the action;
making a third determination that the baby has prematurely awoken;
causing, in response to the third determination, the first sound to emit and a volume of the first sound to increase until the volume is a first predetermined volume or until the baby falls asleep again;
making a fourth determination that the baby has fallen asleep again; and
causing, in response to the fourth determination, the volume to decrease until the volume is a second predetermined volume or until the baby reaches the predetermined state again.

17. The method of claim 16, further comprising:
causing, in response to the third determination, the first light to emit; and
causing, in response to the fourth determination, the first light to stop emitting.

18. The method of claim 16, further comprising further transmitting the third electrical signal to decrease the action.

19. The method of claim 16, further comprising further transmitting the third electrical signal to cancel the action.

20. A computer program product comprising instructions that are stored on a non-transitory computer-readable medium and that, when executed by a processor, cause an apparatus to:
obtain a sleep schedule of a baby;
obtain vitals of the baby, wherein the vitals are based on pulse oximetry;
transmit, when the sleep schedule indicates that the baby is to begin sleep, a first electrical signal to cause an action, wherein the action is an emission of a first sound or a first light;
make, based on the vitals and after transmitting the first electrical signal, a first determination that the baby has fallen asleep;
transmit, in response to the first determination, a second electrical signal to adjust the action;
make, based on the vitals and after transmitting the second electrical signal, a second determination that the baby has reached a predetermined state of sleep;
transmit, in response to the second determination, a third electrical signal to further adjust or cancel the action;
make a third determination that the baby has prematurely awoken;
cause, in response to the third determination, the first light to emit;
make a fourth determination that the baby has fallen asleep again; and
cause, in response to the fourth determination, the first light to stop emitting.

21. The computer program product of claim 20, wherein the instructions further cause the apparatus to:
cause, in response to the third determination, the first sound to emit and a volume of the first sound to increase until the volume is a first predetermined volume or until the baby falls asleep again; and
cause, in response to the fourth determination, the volume to decrease until the volume is a second predetermined volume or until the baby reaches the predetermined state again.

22. The computer program product of claim 20, wherein the instructions further cause the apparatus to further transmit the third electrical signal to decrease the action.

23. A baby monitor system comprising:
a memory; and
a processor coupled to the memory and configured to:
transmit, in response to a manual toggle or a manual instruction when a baby is to sleep, a first electrical signal to cause an action, wherein the action is an emission of a first sound or a first light;
obtain, after transmitting the first electrical signal, vitals of the baby, wherein the vitals are based on pulse oximetry;
make, based on the vitals, a first determination that the baby has fallen asleep;
transmit, in response to the first determination, a second electrical signal to adjust the action;
make, based on the vitals and after transmitting the second electrical signal, a second determination that the baby has reached a predetermined state of sleep,
transmit, in response to the second determination, a third electrical signal to further adjust or cancel the action;
make a third determination that the baby has prematurely awoken;
cause, in response to the third determination, either the first light to emit or both the first sound to emit and a volume of the first sound to increase until the volume is a first predetermined volume or until the baby falls asleep again;
make a fourth determination that the baby has fallen asleep again; and
cause, in response to the fourth determination, either the first light to stop emitting or the volume to decrease until the volume is a second predetermined volume or until the baby reaches the predetermined state again.

* * * * *